(12) United States Patent
Sarantaridis et al.

(10) Patent No.: US 8,894,837 B2
(45) Date of Patent: Nov. 25, 2014

(54) ELECTROCHEMICAL DETECTION OF PARTICULATES IN A GASEOUS SAMPLE USING POTENTIOMETRIC MEASUREMENTS IN A GASEOUS FLAME ELECTROLYTE

(75) Inventors: Dimitrios Sarantaridis, London (GB); Daren J. Caruana, London (GB)

(73) Assignee: UCL Business PLC (GB)

( * ) Notice: Subject to any disclaimer, the term of this patent is extended or adjusted under 35 U.S.C. 154(b) by 268 days.

(21) Appl. No.: 13/511,286

(22) PCT Filed: Nov. 23, 2010

(86) PCT No.: PCT/GB2010/002162
§ 371 (c)(1),
(2), (4) Date: Sep. 12, 2012

(87) PCT Pub. No.: WO2011/061517
PCT Pub. Date: May 26, 2011

(65) Prior Publication Data
US 2012/0325684 A1    Dec. 27, 2012

(30) Foreign Application Priority Data

Nov. 23, 2009   (GB) .................................. 0920526.1

(51) Int. Cl.
*G01N 27/416*        (2006.01)
*G01N 27/66*         (2006.01)
*G01N 15/06*         (2006.01)

(52) U.S. Cl.
CPC ............ *G01N 27/4161* (2013.01); *G01N 27/66* (2013.01); *G01N 15/0656* (2013.01)

USPC ......................... 205/792; 205/775; 204/412

(58) Field of Classification Search
USPC ................ 204/400; 205/775; 422/68.1, 82.01
See application file for complete search history.

(56) References Cited

U.S. PATENT DOCUMENTS

| 7,573,571 B2 | 8/2009 | Creek et al. |
| 2002/0016068 A1 | 2/2002 | Nakano et al. |
| 2003/0044997 A1 | 3/2003 | Kasahara et al. |
| 2009/0137423 A1* | 5/2009 | Higson ........................... 506/12 |

FOREIGN PATENT DOCUMENTS

| WO | WO 01/89024 | 11/2001 |
| WO | WO 2004/061418 | 7/2004 |
| WO | WO 2005/059513 | 6/2005 |

OTHER PUBLICATIONS

Sarantaridis et al. (Chem. Sci., 2012, 3, 2210).*
Hadzifejzovic et al. (Phys. Chem. Chem. Phys., 2006, 8, 2797-2809).*
Caruana et al., "Electrochemistry in Flames: A Preliminary Communication", Electrochemistry Communications, Aug. 31, 2000, 2, 816-821.
Caruana et al., "Gas Phase Electrochemical Detection of Single Latex Particles", Analyst, Jul. 16, 2003, 128, 1286-1290.

(Continued)

*Primary Examiner* — Jennifer Dieterle
(74) *Attorney, Agent, or Firm* — Baker & Hostetler LLP (57) ABSTRACT

The present invention provides a method for the detection of particulates in a sample, wherein the particulates are introduced into a plasma and the potential difference between a common electrode and each of a plurality of indicator electrodes is measured. The invention further provides an electrode array and an apparatus which can be used for the potentiometric detection of particulates in a sample.

19 Claims, 6 Drawing Sheets

(56) References Cited

OTHER PUBLICATIONS

Dimitrakopoulos et al., "Evaluation of a Four Sensor Array Used in a Wall-Jet Configured Flow Cell for Flow Injection Potentiometry", Electroanalysis, 2001, 13(2), 161-163.

Jaber et al., "Action Potential Recording from Dielectrophoretically Positioned Neurons inside Micro-Wells of a Planar Microelectrode Array", Journal of Neuroscience Methods, 2009, 182, 255-235.

Talbot et al., "Characteristic Fragmentation of Bacteriopanepolyols During Atmospheric Pressure Chemical Ionisation Liquid Chromatography/Ion trap Mass Spectrometry", Rapid Commun. Mass Spectrom, Oct. 2003, 17, 2788-2796.

Galiani et al., "Plasma Electrochemistry: Absorption of Flame Borne Species in Platinum Electrodes", Electrochimica Acta, 2008, 53, 3271-3278.

* cited by examiner

ELECTROCHEMICAL DETECTION OF PARTICULATES IN A GASEOUS SAMPLE USING POTENTIOMETRIC MEASUREMENTS IN A GASEOUS FLAME ELECTROLYTE

CROSS-REFERENCE TO RELATED APPLICATIONS

This application is the National Stage of International Application No. PCT/GB2010/002162, filed Nov. 23, 2010, which claims the benefit of Great Britain Application No. 0920526.1, filed Nov. 23, 2009, the disclosures of which are incorporated herein by reference in their entireties.

The present invention relates to a method for the detection of particulates in a gaseous sample and an electrode arrangement and apparatus for said detection.

Traditionally, electrochemical analysis is confined to liquid or solid media containing stable mobile ionic species. Recently, Caruana and McCormack (*Electrochem Commun.*, 2000 (2) 816-821) have shown a flame plasma to be suitable as an electrolyte for supporting electrochemical measurements.

Furthermore, conductivity measurements are well established for measuring changes in ionic concentrations in a flame plasma, and have been successfully used for gas chromatography detection.

U.S. Pat. No. 7,573,571 describes a method and apparatus for the detection of particulates. In particular, this document describes a method and apparatus for rapid and accurate detection and discrimination of biological, radiological, and chemical particles in air. A suspect aerosol of the target particulates is treated with a taggant aerosol of ultrafine particulates. Coagulation of the taggant and target particles causes a change in fluorescent properties of the cloud, providing an indication of the presence of the target. However, taggant aerosol is expensive and the technique requires a laser, which is also expensive and requires extensive safety precautions. Furthermore, each type of taggant will only bind to a certain target molecule, meaning that to detect different particles different taggant types are required which increases the complexity of the analysis.

Therefore, there is a need for alternative and improved methods for the detection of particulates in a sample and an electrode arrangement and apparatus for said detection.

The object of the present invention is to provide an improved method for the detection of particulates in a sample.

In this regard, the present invention provides a method for the detection of particulates in a sample, comprising (i) introducing the particulates into a plasma; and (ii) measuring the potential difference between a common electrode and each of a plurality of indicator electrodes.

The method of the present invention is advantageous because it is simpler and less expensive than the prior art methods for the detection of particulates. A further advantage of the method of the present invention is that it is more sensitive than the methods of the prior art, being able to distinguish between species of similar magnitudes. A further advantage of the present method is that it can easily detect and identify different species in a mixed species sample. A further advantage of the present application is the amplification achieved, due to the break down of one particulate into many others, followed by detection to enable particulate identification.

It is a further object of the present invention to provide a potentiometric electrode arrangement for the detection of particulates in a sample.

In this regard, the present invention provides a potentiometric electrode arrangement for the detection of particulates in a sample, comprising a common electrode and a plurality of indicator electrodes.

The electrode arrangement of the present invention is advantageous because it is simpler and less expensive than the prior art systems for the detection of particulates. A further advantage of the electrode arrangement of the present invention is that it is more sensitive than the arrangements of the prior art, being able to distinguish between species of similar magnitudes. A further advantage of the present electrode arrangement is that it can easily detect and identify different species in a mixed species sample.

It is a further object of the present invention to provide a potentiometric apparatus for the detection of particulates in a sample.

In this regard, the present invention further provides a potentiometric apparatus for the detection of particulates in a sample, comprising (i) a means arranged to introduce the particulates into a plasma; and (ii) a common electrode and a plurality of indicator electrodes, wherein the electrodes are positioned to measure the potential difference between the common electrode and each of the plurality of indicator electrodes in the plasma.

The apparatus of the present invention is advantageous because it is simpler and less expensive than the prior art systems for the detection of particulates. A further advantage of the apparatus of the present invention is that it is more sensitive than the apparatuses of the prior art, being able to distinguish between species of similar magnitudes. A further advantage of the present apparatus is that it can easily detect and identify different species in a mixed species sample. A further advantage of the apparatus of the present invention is that it could be made into a portable device because plasmas, in particular flames are stable and easy to control.

The present invention further provides the use of an electrode arrangement or an apparatus according to the present invention for the potentiometric detection of particulates in a sample.

The present invention provides a potentiometric method, arrangement and apparatus. A potentiometric technique uses electrodes to determine the concentration of certain components in a sample by measuring the electrical potential of an electrode when no current is flowing. The signal is measured as the potential difference, or voltage, between an indicator electrode and a common electrode.

In contrast, an amperometric technique determines the concentration of an analyte by measurement of the current generated in a suitable chemical reaction. In particular, a constant or varying potential is applied at an electrode surface and the resulting current is measured, usually using a three electrode system. Amperometric techniques are also used to measure the change in local conductivity in a conductivity probe.

Potentiometric techniques are advantageous because the passive potential measurements taken have a minimal effect on the medium between the electrodes. In particular, amperometry can introduce stray electric fields that can distort the plasma leading to erroneous measurements. Amperometric devices comprising a plurality of electrodes, e.g. an array, could not be used to produce meaningful potentiometric measurements in the present invention because such a device would produce a single average potential difference measurement. A single average potential difference measurement cannot be used to distinguish between different types of particulates, as demonstrated in the examples of this application.

As used herein, the "indicator electrode" is an electrode whose potential will depend on the concentration of the fragmentation products of the particulates present in the sample.

As used herein, the "common electrode" is an electrode which provides a defined common potential against which the potential of each of the indicator electrodes is measured. This may be any suitable electrode that is in contact with the plasma.

The method of the present invention may be used to detect particulates in a number of different samples. The samples may be aerosol samples or gaseous samples.

In the method of the present invention, the particulates are introduced into a plasma. The particulates are fragmented in the plasma to form fragmentation products. In the case of a flame plasma, the fragmentation products are combustion products.

As used herein, a "plasma" is an excited state of matter, similar to a gas, that contains non-bonded charged species. The charged species may be positive ions, negative ions, radicals and/or electrons. The plasma may be any plasma with which the skilled person is familiar. In particular, the plasma may be selected from the group consisting of low pressure plasmas and atmospheric plasmas. Examples of low pressure plasmas include, but are not limited to, glow discharge plasma (direct current (DC) or radio frequency ((RF)), capacitively coupled plasma (RF), inductively coupled plasma (RF) and wave heated plasma (RF or microwave frequency (MW)). Examples of atmospheric pressure plasmas include, but are not limited to, flame plasma, arc discharge plasma, corona discharge plasma, dielectric barrier discharge plasma and capacitive discharge plasma (RF). In one embodiment, the plasma is a flame plasma.

The invention will now be described in detail with reference to one embodiment wherein the plasma is a flame plasma. As used herein, a "flame plasma" is the medium present within a flame. Flames are considered to be weak plasmas which are overall neutral. The flame plasma contains mobile charged carriers mainly free electrons and atomic or molecular cations (e.g. $H_3O^+$) which renders the flame plasma electrically conducting. For this reason, the flame plasma can be suitable as an electrolyte for supporting electrochemical measurements.

In one embodiment of the present invention, the flame plasma is produced by the ignition of a combustible gaseous stream. The means for providing a combustible gaseous stream may be any type of burner. As used herein, a burner comprises a vertical metal tube connected to a gas source. Optionally, burners may include adjustable holes at the base to allow air into the gas source. Optionally, the burner may be water-cooled. Examples of suitable burners for use in the present invention include a Méker burner, a Bunsen burner, or any other burner capable of sustaining a stable premixed or diffusion flame, e.g., flat flame, opposed jet flame etc. A Méker burner is particularly advantageous as it provides a laminar flow and a uniform chemical environment through its horizontal cross-section.

In one embodiment of the present invention, the common electrode may be the burner top-plate. The burner top-plate may be constructed from an electrically conducting or semi-conducting material, e.g. stainless steel or other alloy resistant to high temperature oxidation.

The combustible gaseous stream may be supplied in a single stream. Alternatively, the combustible gaseous stream may be supplied in a plurality of independent streams, e.g. 2, 3, 4, 5, etc streams. In one embodiment, the combustible gaseous stream may be supplied in two independent streams.

The use of a plurality of independent streams is advantageous because the point at which the particulates are introduced may be precisely controlled.

Ignition of the combustible gaseous stream may be carried out by any suitable method, e.g. an initial spark after which the flame continues to burn with a stable flame plasma provided the combustible gaseous stream is flowing.

The combustible gaseous stream may comprise at least one combustible gas, e.g. a fuel such as hydrogen or methane, and optionally an oxidiser such as oxygen or air. These gases may optionally be mixed with a diluent gas such as nitrogen or argon. In one embodiment, the combustible gaseous stream comprises $H_2/O_2/N_2$. The $H_2/O_2/N_2$ may be present in any ratio that can sustain a flame, e.g. a 2:1:1 ratio.

The introduction of the particulates into the flame plasma may be carried out by any suitable method, e.g. direct introduction of the particulates into the flame plasma or creation of a product stream comprising the particulates and the gases present in the combustible gaseous stream, wherein the product stream, which comprises the combustible gaseous stream, is then ignited.

As used herein, the "product stream" is the combination of the combustible gaseous stream and the particulates.

In one embodiment, the particulates may be introduced directly into the flame plasma through one or more capillary tubes. The particulates may be introduced into the flame plasma in a separate gaseous stream or in the form of a spray or a solution.

When the particulates are introduced directly into the flame plasma, the means arranged to introduce the particulates may be one or more capillary tubes with nozzles that allows the particulates to be directly introduced to the flame plasma. The tubes and nozzles may be made out of any suitable material, but are preferably made from metal to withstand the heat of the flame plasma.

The capillary tube(s) may be independent of the burner. Alternatively, the capillary tube(s) may be integral with the burner. When the capillary tube(s) is integral with the burner, it may be arranged to introduce the particulates through one or more holes in the burner top-plate. These holes may be arranged among the holes through which the combustible gaseous stream is supplied.

When the particulates are formed into a product stream prior to introduction into the flame plasma, the particulates may be comprised in a separate gaseous or aerosol stream which is then mixed with one or more of the gases present in the combustible gaseous stream to form the product stream. When the combustible gaseous stream comprises more than one type of gas, the particulates may be introduced into one of the gases prior to mixing with the other gases to form the product stream. Alternatively, two or more of the gases may be combined with the particulates prior to mixing with the other gases to form the product stream.

The introduction of the particulates into the combustible gaseous stream is advantageous as it can provide improved mixing of the particulates and the combustible gaseous stream prior to ignition which may lead to a more uniform distribution of the particulates within the product stream leading to improved detection.

The introduction of the particulates directly into the flame plasma is advantageous as it allows the precise position at which the particulates are introduced into the flame plasma to be ascertained. This is important for accurate analysis of the shape of the plume of combustion products, which is dependent on how long the combustion products have been in the flame plasma, which in turn depends on the position at which the particulates are introduced into the flame plasma.

The potentiometric apparatus of the present invention comprises a means arranged to introduce the particulates into a flame plasma, which may be provided when the combustible gaseous stream is ignited. In one embodiment, the means is arranged to introduce the particulates into a flame plasma in order to fragment the particulates. As discussed above, the particulates may be introduced into the flame plasma in a number of different ways.

When the particulates are introduced through the creation of a product stream, the means arranged to introduce the particulates may be a tube which links to a tube supplying the combustible gaseous stream such that the particulates are introduced to the combustible gaseous stream. A valve may be present between the two tubes such that the user may choose when the particulates are introduced.

Alternatively, when the particulates are in the liquid phase, the means arranged to introduce the particulates may be a nebulizer attached to a tube supplying the combustible gaseous stream. When the particulates are airborne particulates, they may be dissolved in a liquid prior to analysis in order to use a nebulizer. The nebulizer converts the particulates into an aerosol which is then introduced into the gaseous stream. It is advantageous to convert the particulates into an aerosol prior to analysis because the particulates in the aerosol will be less compact, i.e. there will be a lower density of particulates. This provides improved detection as the particulates will be less densely packed as they enter the flame plasma.

When the particulates are introduced into one, or a combination, of the gases prior to mixing of the gases to form the product stream, the means arranged to introduce the particulates may be a tube which links to a tube supplying the one, or the combination of, gaseous stream gases such that the particulates are introduced to the one, or the combination of, gases. A valve may be present between the two tubes such that the user may choose when the particulates are introduced. Alternatively, the means arranged to introduce the particulates may be a nebulizer attached to a tube supplying the one, or the combination of, gaseous stream gases. The nebulizer converts the particulates into an aerosol which is then introduced into the one, or the combination of, gaseous stream gases.

The potentiometric apparatus of the present invention may comprise a means for providing a combustible gaseous stream, wherein the combustible gaseous stream is ignitable to produce a flame plasma. When the combustible gaseous stream comprises $H_2/O_2/N_2$, this means may be a first container containing oxygen, a second container containing hydrogen, a third container containing nitrogen, a mixing chamber where the gases are mixed to form the combustible gaseous stream and a means for transporting the oxygen, hydrogen and nitrogen to the mixing chamber. The mixing chamber may have a blowback protector to avoid the combustible gaseous stream being blown back towards the first, second and third containers. When the combustible gaseous stream comprises $H_2/O_2/N_2$, these gases may be delivered from the first, second, and third containers at flow rates of about 0.1 to about 3.0 L min$^{-1}$, e.g. about 0.5 to about 2.5 L min$^{-1}$, about 1.0 to about 2.0 L min$^{-1}$, e.g. about 1.6 L min$^{-1}$, of $H_2$, about 0.1 to about 3.0 L min$^{-1}$, e.g. about 0.5 to about 2.5 L min$^{-1}$, about 0.5 to about 2.0 L min$^{-1}$, about 0.5 to about 1.5 L min$^{-1}$, e.g. about 0.7 L min$^{-1}$ of $O_2$ and about 0.1 to about 3.0 L min$^{-1}$, e.g. about 0.5 to about 2.5 L min$^{-1}$, about 1.0 to about 2.0 L min$^{-1}$, e.g. about 1.0 L min$^{-1}$ $N_2$.

Without wishing to be bound by theory, the particulates disintegrate at a rate which is dependent on the composition of the particulate material and density. The plume of combustion products increases in size due to gasification of the particulate as it moves from the primary reaction zone, where most of the combustion takes place, to the secondary reaction zone where the combustion field will be separated due to space charge effects within the plume of combustion products. The plume of combustion products will then be detected at the plurality of indicator electrodes, e.g. the multi electrode array, down stream. For example, the predicted increase in volume of the plume of combustion products due to complete combustion (main products: $CO_2$ and $H_2O$) of a single 3 µm diameter ($1.4 \times 10^{-8}$ µl) polystyrene particle at 2400 K will be to approximately 4.4 mm diameter combustion field (or 45 µl), assuming a particle density of 1 g cm$^{-3}$. The expansion of the plume of combustion products is dependent on the particle itself, the flame plasma temperature and fuel/oxidant ratio.

The mechanism of disintegration of the particulates is highly dependent on the physical properties of the particulate and therefore can be used for identification (H. M. Talbot, et al., (2003) 17, 2788-2796). For example, compact high density particulates will take longer to burn and have a different fragmentation profile to particulates which are less dense and loosely packed. The plume of combustion products expands in two dimensions, X and Y, due to space charge effects, and is resolved with time, to aid identification of different particulates by the unique plume of combustion products shape, measured by the plurality of indicator electrodes.

The potential difference response is dominated by the charge separation between the large low mobility cations from the particulate combustion, and the highly mobile electrons. The difference in electrical mobility between the cations and electrons dictates the magnitude of the potential difference. The end result is a three dimensional map of the plume of ionised fragments from the particulate in real time. This will provide a unique fragmentation signature for different particulates.

The potential difference measured in the flame plasma is a mixed potential which may be contributed to by a number of different potentials, e.g. a diffusion potential, a redox potential and a contact potential. The magnitude of the diffusion (or junction) potential measured between two electrodes in a flame plasma is due to the difference in mobility between the anions and cations. In this case the main charge carriers are electrons and cations, the diffusion potential, $\Delta\phi_{Diff}$, is given by the Henderson equation (A. J. Bard and L. Faulkner, Electrochemical Methods: Fundamentals and Applications, 2nd Ed., J. Wiley & Sons, NJ, 2001, p 73):

$$\Delta\phi_{Diff} = \frac{\sum_i \frac{|z_i|u_i}{z_i}(n_i^\alpha - n_i^\beta)}{\sum_i |z_i|u_i(n_i^\alpha - n_i^\beta)} \frac{RT}{F} \ln \frac{\sum_i |z_i|u_i(n_i^\beta)}{\sum_i |z_i|u_i(n_i^\alpha)} \qquad (2)$$

Where $n_i$ is the concentration of the ions or electrons, $z_i$ is the charge on the respective ions and $u_i$ is the mobility of the ions in phases $\alpha$ and $\beta$. The Henderson equation may be applied to the system assuming the following: all the ions behave ideally, only the metal mono-cations and free electrons contribute to the diffusion potential, the flux across the junction was in a steady state, and the electroneutrality was conserved. The mobility values for electrons and $CHO^+$ ions in flame plasma are 4000 cm$^2$ V$^{-1}$ s$^{-1}$ and 15 cm$^2$ V$^{-1}$ s$^{-1}$, respectively. Using these estimated values for ion mobility, the magnitude as given by the Henderson equation will be between 0.1 and 0.4 V, depending on the various concentrations of electrons and cations.

The mixed potential results from the presence of two reactions on an electrode surface which results in charge transfer. When the electrolyte contains free electrons and ions, the mode of conductivity may be electronic or ionic and the potential may be considered as a mixed potential, defined by two surface reactions $e^-_{(g)} = e^-_{(el)}$, and $M^+_{(g)} + e^-_{(el)} = M_{(g)}$, where M is an ionisable metal species added to the flame plasma gases. In electrochemical terms this is a mixed potential.

The potential difference is measured between a common electrode and each of a plurality, i.e. 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100 etc, of indicator electrodes to detect ionisable species in the flame plasma.

In one embodiment, the plurality of indicator electrodes is present as a plurality of independent electrodes. The use of a plurality of independent indicator electrodes is advantageous because it allows the indicator electrodes to be positioned independently within the flame plasma.

Figure 1:
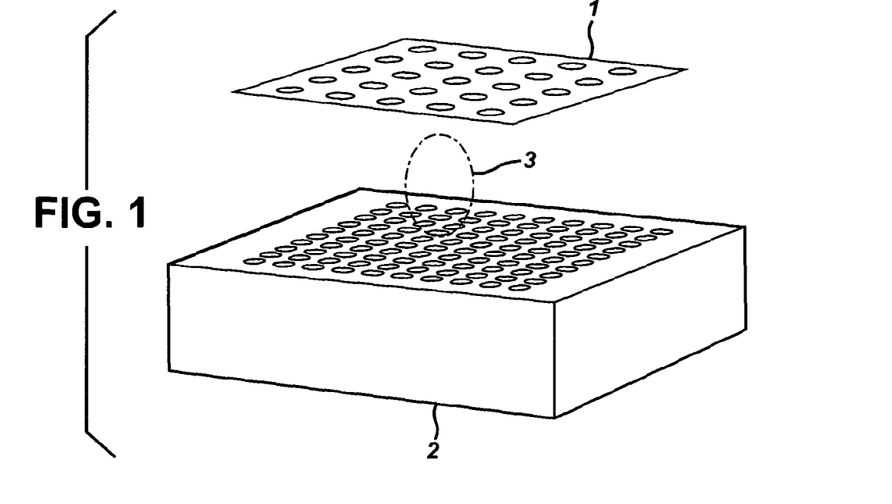
FIG. 1 shows a multi electrode array suitable for use in the present invention.

In an alternative embodiment, the plurality of indicator electrodes may be present in a multi electrode array (1), an example of which is shown in FIG. 1. The multi electrode array comprises a plurality of indicator electrodes set into a sheet of electrically insulating material such as aluminium oxide or suspended by a holder placed outside the flame plasma. The multi electrode array may comprise 2, 4, 6, 8, 10, 12, 14, 16, 18, 20, 28, 32, 40, 50, 56, 60, 64, 76, 80, 88, 96, 100 etc electrodes.

As can be seen from FIG. 1, the plurality of indicator electrodes may be arranged in a regular pattern, although it is also possible to arrange the indicator electrodes irregularly on the multi electrode array. FIG. 1 shows the plume of combustion products (3) produced when the airborne particulate is combusted after it passes through the top-plate of the burner (2). In the embodiment shown in FIG. 1, the burner is a Méker type burner. The use of a plurality of indicator electrodes, in particular in the multi electrode array shown in FIG. 1, allows the shape of the plume of combustion products to be detected in three dimensions (x, y and time).

The use of a plurality of indicator electrodes is advantageous as it provides improved sensitivity and enables the detection and identification of similar particulates. Furthermore, as discussed above, the use of a plurality of electrodes allows the shape of the plume of combustion products to be measured. The shape of the plume of combustion products will be dependent on the properties or the airborne particulate and can therefore be used to identify the particulate. Furthermore, by using a plurality of electrodes, it is possible to detect the number of particulates going through the flame plasma.

Without wishing to be bound by theory, the introduction of the particulates into the flame plasma, e.g. as a plume of combustion products, results in an increase in charged species relative to the surrounding flame plasma. Hydrogen/oxygen flame plasmas are particularly suitable for use in the present invention because the background ionisation is low in this type of flame plasma. The increase in charged species within the flame plasma is detected by measuring the potential difference between a common electrode and each of a plurality of indicator electrodes.

The potential difference may be measured by any technique known to the skilled person, e.g. with a voltmeter having a high input impedance. An example is a buffer amplifier in conjunction with a low input impedance voltmeter, which provides electrical impedance transformation from one circuit to another. In one embodiment, a unity gain buffer amplifier, with an input impedance>1000 MΩ and input capacitance of about 6 pF, providing a measurement time of about 0.6 ms may be used.

In one embodiment, the potential difference is recorded as a function of time and may be stored on a digital storage oscilloscope (e.g. Tektronix, TDS 3012). Measuring the potential difference as a function of time is advantageous because it provides data on the shape of the plume of combustion products which allows improved identification of the particulates.

The common electrode may be manufactured from any suitable material, e.g. any electrically conducting or semiconducting material, e.g. carbon (including doped diamond), platinum or an alloy, metal oxide.

Each of the indicator electrodes may be independently manufactured from any suitable material, e.g. any electrically conducting or semiconducting material, e.g. carbon (including doped diamond), platinum or an alloy, metal oxide, composite carbon or metal containing ceramic based material.

The indicator and common electrodes used herein may be discs set in insulating materials, rods (e.g. wires) or spheres. Rod or sphere electrodes may be held in the flame plasma in a suitable orientation.

The indicator electrodes may be the same or different. In a preferred embodiment, all the indicator electrodes are the same. It is preferred for all the indicator electrodes to be the same because the contact with the flame plasma will be identical and the potential response will be due to the changes in the flame plasma properties due to the combustion products colliding with the electrode. In another embodiment, the indicator electrodes may be different. In one embodiment, at least one indicator electrode is made from a material which is different from a material from which at least one of the other indicator electrodes is made.

The common and indicator electrodes are positioned in the flame plasma in any suitable fashion. When the electrodes are rod or wire electrodes, the indicator electrodes may be positioned parallel to one another. The indicator electrodes may be positioned parallel to one another in a straight line wherein each indicator electrode is between about 0.2 mm and about 7.0 mm, e.g. between about 0.5 mm and about 6.5 mm, between about 0.8 mm and about 6.5 mm, between about 1.0 mm and about 6.5 mm, between about 2.0 mm and about 6.5 mm, between about 2.5 mm and about 6.5 mm, between about 3.0 mm and about 6.0 mm, between about 3.0 mm and about 5.0 mm, e.g. about 0.2 mm, about 0.5 mm, about 1.0 mm, about 2.0 mm, about 2.5 mm, about 3.0 mm, about 3.5 mm, about 4.0 mm, about 4.5 mm, about 5.0 mm, about 5.5 mm, about 6.0 mm or about 6.5 mm, from its neighbouring indicator electrode. Alternatively, the indicator electrodes may not be positioned parallel to one another.

When the indicator electrodes are rod or wire electrodes, they may be arranged such that the ends of the electrodes form a square or a hexagon.

The vertical height of each of the indicator electrodes from the flame front may independently be from about 3.0 mm to about 20.0 mm, e.g. from about 5.0 mm to about 18.0 mm, between about 10.0 mm and about 15.0 mm, between about 12.0 mm and about 15.0 mm. This height range is advantageous when detecting particulates such as bacteria, viruses, pollen grains and dust as it provides the highest chance of detection.

In one embodiment, some or all of the indicator electrodes may be positioned at the same height from the bottom of the flame. Positioning all the indicator electrodes at the same height is preferred because it allows a more accurate measurement of the shape of the plume of combustion products.

In particular, if the indicator electrodes are positioned at different heights from the bottom of the flame, the shape of the plume of combustion products may be distorted by the indicator electrodes positioned lower in the flame, such that the indicator electrodes positioned higher in the flame may provide erroneous readings.

When a burner is used, e.g. a Méker burner, the bottom of the flame is defined as the burner top plate (i.e. the end of the tube(s) where the combustible gaseous stream exits).

Figure 2A:
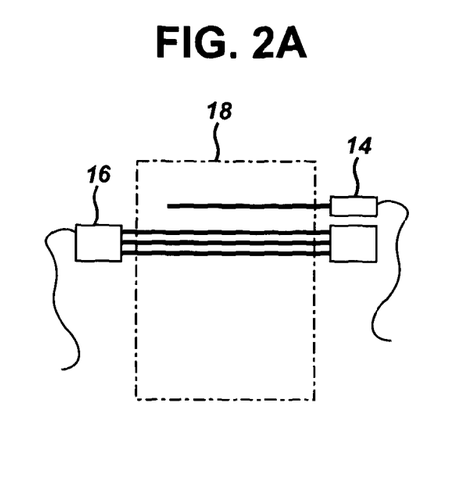
FIG. 2 shows a schematic of offset indicator electrodes.
Figure 2B:
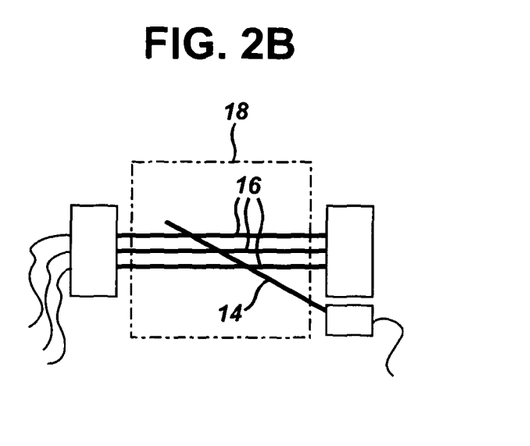

Alternatively, the indicator electrodes may all be positioned at different heights from the bottom of the flame. In one embodiment, the indicator electrodes may be positioned offset to one another as shown in FIG. 2A. In particular in FIG. 2A, the front view shows that the indicator electrodes (16) are vertically offset in the flame plasma (18). The common electrode (14) is also shown. The top view in FIG. 2B shows that the indicator electrodes (16) are also horizontally offset in the flame plasma (18).

The common electrode may be positioned higher in the flame than the indicator electrodes or lower in the flame than the indicator electrodes. If the plurality of indicator electrodes is positioned at the same height in the flame, the common electrode may be positioned at the same height in the flame as the indicator electrodes. If the indicator electrodes are positioned at different heights in the flame, the common electrode may be positioned at any height which lies within the range of heights of the indicator electrodes.

It is advantageous for the common electrode to be positioned equidistant from all the indicator electrodes. For this reason, it is useful to use a flat plate or mesh common electrode or the burner top plate. It is also advantageous to position the common electrode higher in the flame than the plurality of indicator electrodes so that the common electrode does not distort the shape of the plume of combustion products.

Each of the indicator electrodes may be coated. Suitable coatings include dissimilar metal, ceramic composite, metal oxide or nitride. In one embodiment, all of the indicator electrodes are coated. Coating the indicator electrodes may be advantageous as this will improve the sensitivity of the electrodes by making the electrodes more responsive to the breakdown products of combustion of the particulates and improve the life time of the electrodes against aging or degradation.

The common electrode may be coated. Suitable coatings include dissimilar metal or conducting material, ceramic composite, metal oxide metal or alloy. Coating the common electrode may advantageously provide a stable potential over time to reduce the effects of aging or degradation.

Each indicator electrode may independently have the dimensions (surface area) of about $0.1 \text{ mm}^2$ to about $50.0 \text{ mm}^2$, e.g. about $0.1 \text{ mm}^2$ to about $40.0 \text{ mm}^2$, about $0.1 \text{ mm}^2$ to about $30.0 \text{ mm}^2$, about $0.1 \text{ mm}^2$ to about $25.0 \text{ mm}^2$, about $0.1 \text{ mm}^2$ to about $20.0 \text{ mm}^2$, about $0.1 \text{ mm}^2$ to about $10.0 \text{ mm}^2$, about $0.1 \text{ mm}^2$ to about $5.0 \text{ mm}^2$, about $0.1 \text{ mm}^2$ to about $3.0 \text{ mm}^2$, about $0.5 \text{ mm}^2$ to about $2.5 \text{ mm}^2$, about $1.0 \text{ mm}^2$ to about $2.0 \text{ mm}^2$. In one embodiment, all the indicator electrodes have the same dimensions.

The common electrode may have the dimensions (surface area) of about $0.1$ to about $50 \text{ mm}^2$ e.g. about $0.1$ to about $20 \text{ mm}^2$ and can be a wire mesh or plate and can span the entire flame.

The particulates which can be detected using the method, arrangement and apparatus of the present invention are ionisable particulates, e.g. airborne particulates. In particular, the method, arrangement and apparatus of the present invention are useful in detecting biological and non-biological particulate species. The present method, arrangement and apparatus are particularly useful for detecting airborne particulates selected from the group consisting of bacteria, bacterial spores, viruses, pollen grains, secondary organic aerosols and dust.

The present invention is suitable for the detection of bacteria selected from the group consisting of *Bacillius subtilis, Bacillus anthracis* (Anthrax) *Bartonella quintana* (Trench fever) *Clostridium botulinum* (Botulism) and their spores, and *Rickettsia rickettsii* (Rocky Mountain spotted fever) *Salmonella typhi* (Typhoid) which are non spore forming and can be detected in an aerosol.

The present invention is suitable for the detection of viruses selected from the group consisting of *Bartonella quintana* (Trench fever), Dengue fever virus, Ebola virus.

The present invention is suitable for the detection of pollen grains selected from the group consisting of Birch Pollen, ragweed, Goldenrod Pollen, Pine Pollen, grass spores, black walnut pollen.

Although the present invention has been described with reference to an embodiment wherein the plasma is a flame plasma, the skilled person will understand that the invention is not limited to the use of flame plasma and that a different plasma, such as glow discharge plasma (direct current (DC) or radio frequency ((RF)), capacitively coupled plasma (RF), inductively coupled plasma (RF), wave heated plasma (RF or microwave frequency (MW)), flame plasma, arc discharge plasma, corona discharge plasma, dielectric barrier discharge plasma or capacitive discharge plasma (RF) may be used in place of the flame plasma as described above.

The present invention is now described, by way of illustration only, with reference to the accompanying drawings, in which:

FIGS. 10(*a*) to 10(*d*) show 2D plots of the time-dependent potential differences for (a) Bermuda pollen, (b) Black walnut pollen, (c) Bermuda spore and (d) Johnson grass Spore FIG. 3 shows a schematic diagram of an apparatus of the present invention. The burner (2) used was an air-cooled Méker type burner fed by one gaseous stream of $H_2/O_2/N_2$ (4, 6). The burner top-plate has an arrangement of two groups of 19 holes of 0.5 mm in diameter, arranged [3,4,6,4,3] in a regular hexagonal array. The gases $H_2/O_2/N_2$ were delivered at $H_2$ (1.6 L min$^{-1}$)/$O_2$ (0.7 L min$^{-1}$)/$N_2$ (1.0 L min$^{-1}$) (all gases used were at 99.9+% assay supplied by BOC, UK) controlled by electronic mass flow controllers (supplied by Brooks UK) producing a stable fuel lean flame, approximately 1 cm in diameter and 6 cm high at atmospheric pressure.

Figure 3:
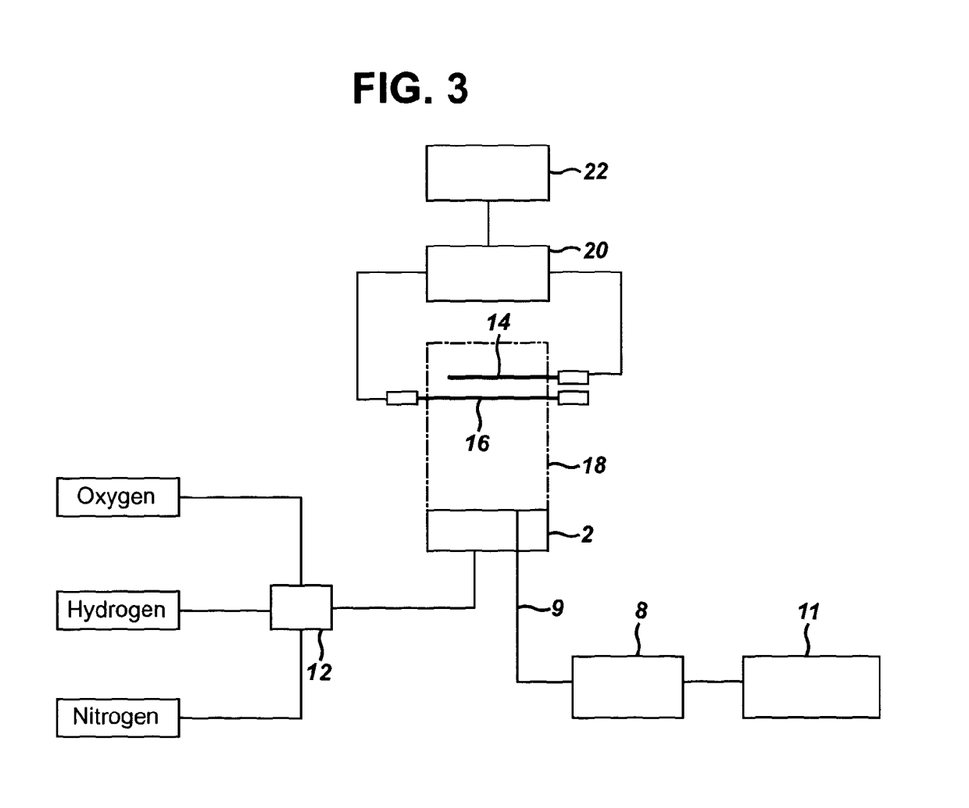
FIG. 3 shows a schematic diagram of an apparatus of the present invention.

The nitrogen, hydrogen and oxygen streams were mixed in a mixing chamber (12) with a blowback protector to provide the combustible gaseous stream.

The particulates (8) were introduced through a stainless steel capillary (9) (dimensions 400 μm outer diameter, 150 μm inner diameter) which was fed through a special hole at the centre of the regular array of holes creating the burner. The particulates flow through the capillary in a stream of air introduced by an air syringe pump (11) and straight into the flame plasma. The particulates were introduced into the air stream using a shaking sample container containing dry particulates. The dry air was supplied through the syringe pump (11) at a constant flow rate (1-2 ml min$^{-1}$)

The burner was mounted vertically on an earthed aluminium table. The common and indicator electrodes (14, 16) were positioned in the flame plasma (18) using x, y and z micropositioner platforms, with the horizontal axis of each platform motorised (PI, supplied by Lambda Scientific, UK) and controlled remotely by PC.

The indicator electrodes (16) were positioned 15.0 mm above the burner top plate. The common electrode (14) was positioned 3 mm above the indicator electrodes. The common (14) and indicator (16) electrodes were manufactured from 0.5 mm diameter platinum wire (99.99% from Johnson Matthey) and were 20 mm long.

The potential difference was measured using a unity gain buffer amplifier (20), with an input impedance>1000 MΩ and input capacitance of 6 pF, providing a capacitative resistance product for 100 MΩ source impedance of 0.6 ms. A multi input voltage digital acquisition card (National Instruments, USA) (22) was used to record the potential difference as a function of time.

The electrode temperature was measured using a thermal imaging pyrometer (800-3000 K) model M9100, supplied by Mikron Instrument Company Inc. (USA). The instrument was calibrated to a traceable standard, fitted with a long distance microscope lens supported by Mikrospec R/T 9100 thermal imaging software. The emissivity of platinum at a wavelength of 0.65 μm was 0.3, and the typical instrument error was ±1.3-2.8° C.

Figure 4:
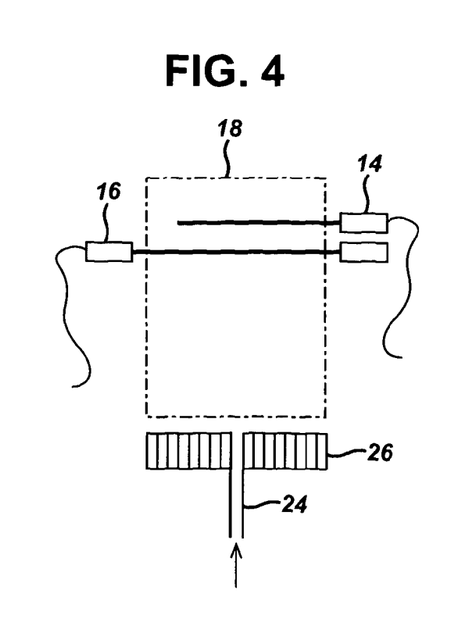
FIG. 4 shows a front view of a first arrangement of the electrodes in the flame plasma.

FIG. 4 shows a front view of the electrodes positioned in the flame plasma (18). The combustible gaseous stream (24) was introduced to the burner to provide the flame plasma (18). The indicator electrodes (16) are positioned closer to the burner top plate compared to the common electrode (14). Furthermore, the indicator electrodes (16) are all positioned at the same height from the burner top plate (26).

Figure 5:
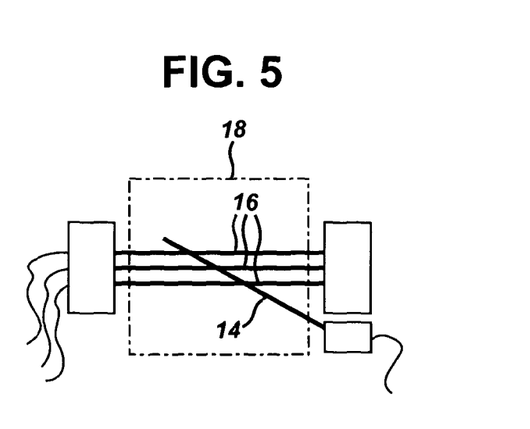
FIG. 5 shows a top view of a first arrangement of the electrodes in the flame plasma.

FIG. 5 shows a top view of the electrodes positioned in the flame plasma (18). The three indicator electrodes (16) are positioned parallel to one another and the common electrode (14) is positioned across the three indicator electrodes (16).

Figure 8:
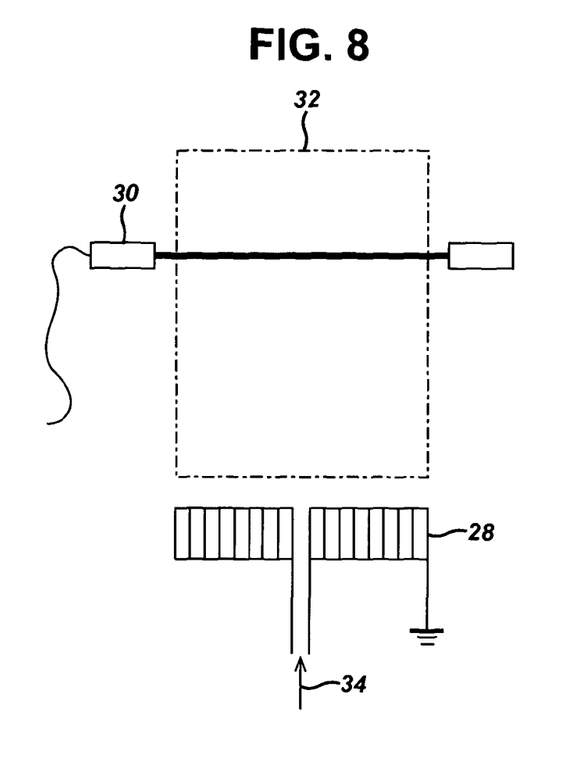
FIG. 8 shows a front view of a second arrangement of electrodes in the flame plasma.

FIG. 8 shows a front view of an alternative embodiment of the invention. The electrodes are positioned in the flame plasma (32). The combustible gaseous stream (34) was introduced to the burner to provide the flame plasma (32). In this embodiment, the burner top plate is used as the common electrode (28). Eight indicator electrodes (30) are positioned in the same plane as the burner top plate. Furthermore, the indicator electrodes (30) are all positioned at the same height from the burner top plate (28).

Figure 9:
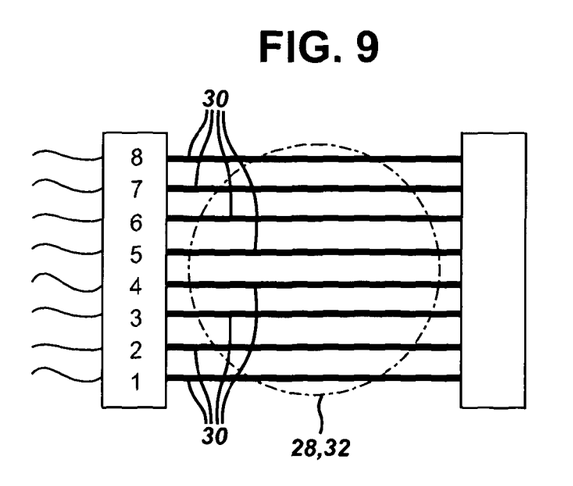
FIG. 9 shows a top view of a second arrangement of electrodes in the flame plasma.
Figure 10A:
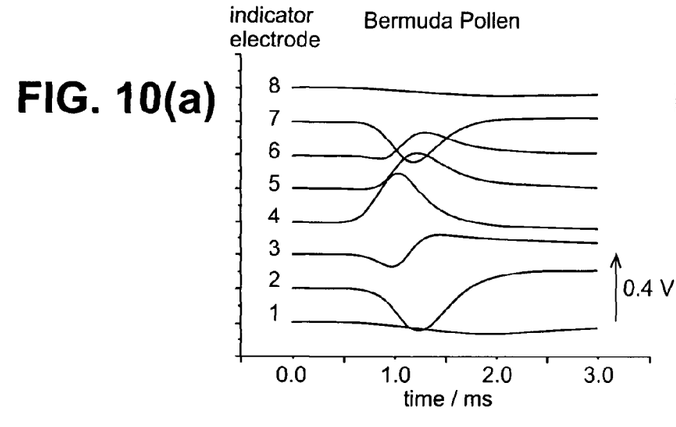
Figure 10B:
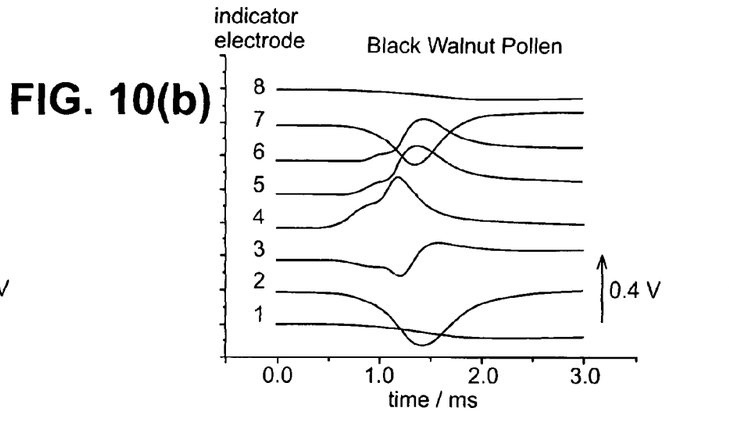
Figure 10C:
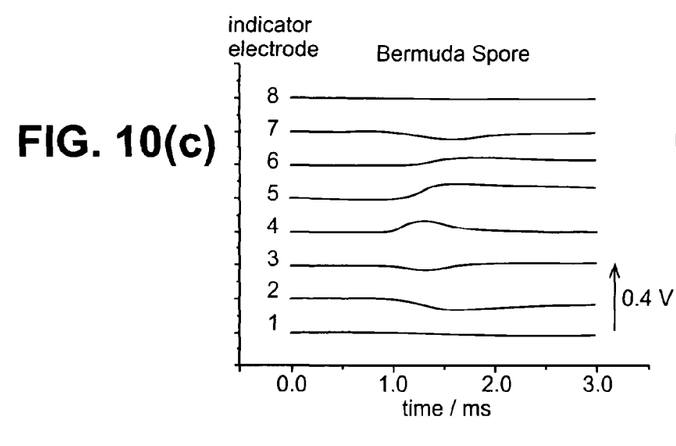
Figure 10D:
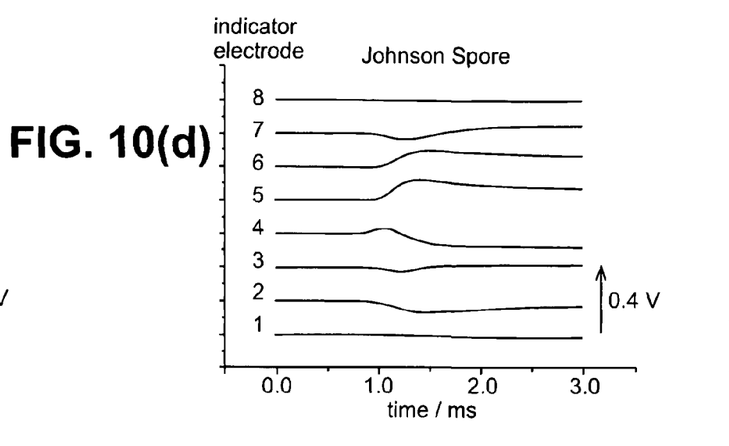

FIG. 9 shows a top view of the electrodes positioned in the flame plasma (32) as illustrated in FIG. 8. The eight indicator electrodes (30) are positioned parallel to one another and the common electrode (28) is the burner top plate (28).

The invention is further illustrated by the following examples. It will be appreciated that the examples are for illustrative purposes only and are not intended to limit the invention as described above. Modification of detail may be made without departing from the scope of the invention.

EXAMPLES

Example 1

Figure 6:
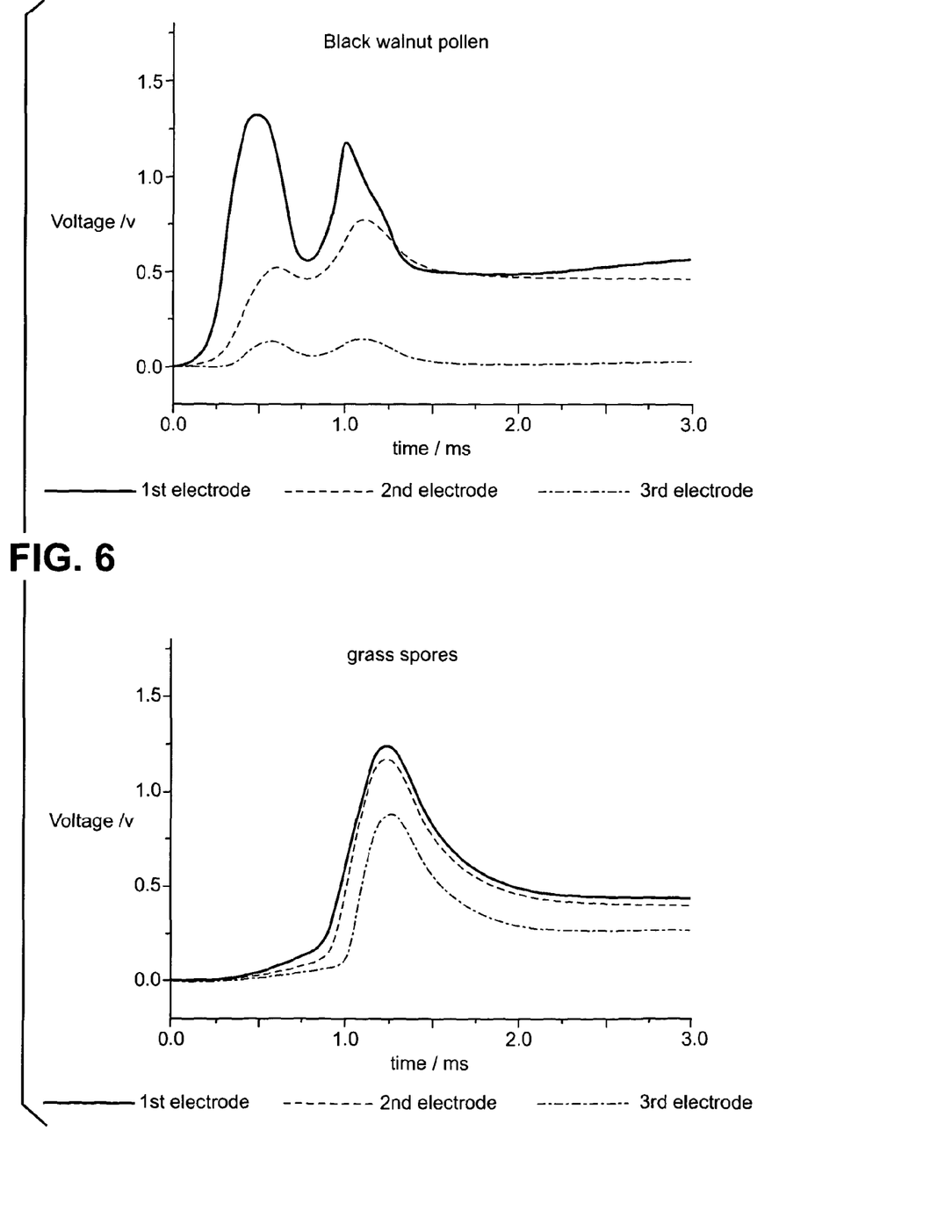
FIG. 6 shows 2-D plots of the time-dependent potential difference for grass spores and black walnut pollen.
Figure 7:
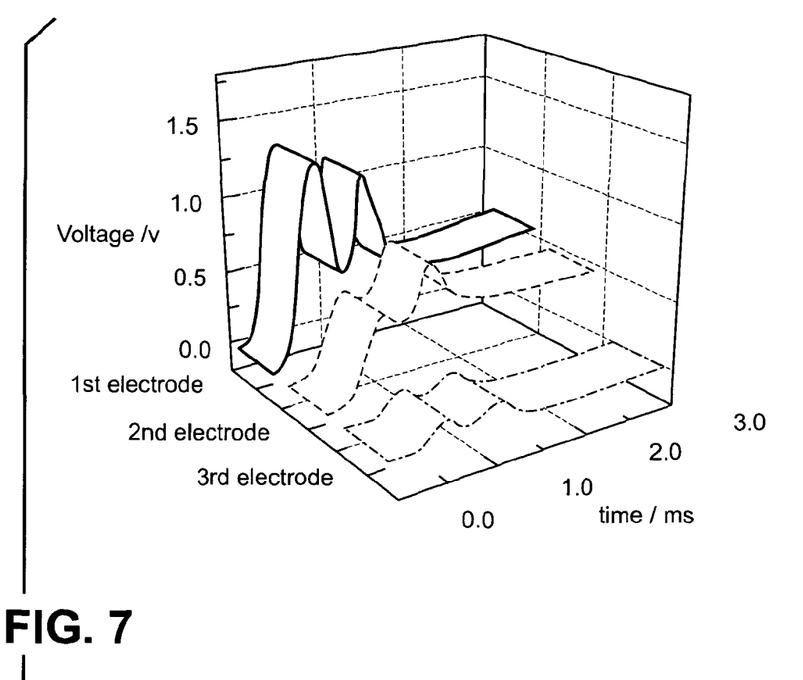
FIG. 7 shows 3-D plots of the time-dependent potential difference for grass spores and black walnut pollen.

Data was collected for grass spores and black walnut pollen using the three indicator electrode system described above. The time-dependent potential difference was recorded for the three parallel indicator electrodes with respect to the fourth common electrode and is illustrated in FIGS. 6 and 7 in 2-D and 3-D. FIGS. 6 and 7 show that for the black walnut pollen there were two events in the 3 ms timeframe, i.e. there were two airborne pollen particulates during this time. However, in the same timeframe, there was a single grass spore event.

FIGS. 6 and 7 show that the potential difference recorded at the first electrode for the grass spore and the black walnut pollen was similar (approximately 1.25 V). Therefore, it would have been very difficult to distinguish between these two particulates using a single indicator electrode system. However, the time-dependent potential differences recorded at the second and third indicator electrodes for these two particulates differ markedly showing how the two species combust in different ways. In particular, the potential difference decreases more quickly when moving from the first to the third indicator electrode for black walnut pollen compared to grass spores. This difference in combustion profile allows grass spores and black walnut pollen to be distinguished using the method, electrode array and apparatus of the present invention.

Example 2

Data was collected for Bermuda pollen (size 21-28 μm), black walnut pollen (size 32 to 41 μm), Bermuda grass spores (size 6 to 8 μm) and Johnson grass spores (size 6 to 9 μm) using the electrode arrangement illustrated in FIGS. 8 and 9. In this particular example, the indicator electrodes were made from nichrome wire (nickel-chromium alloy, 0.5 mm diameter) and the indicator electrodes were positioned approximately 14 mm above the common electrode (burner top plate). Each indicator electrode provided a unique voltage difference with respect to the common electrode. The time-dependent potential difference was recorded for the eight parallel indicator electrodes with respect to the ninth common electrode which was the burner top plate and is illustrated in FIG. 10 in 2D. With reference to the data provided, it can be seen that using the method, electrode array and apparatus of the present invention, it is possible to distinguish between the four different species.

The invention claimed is:

1. A method for the detection of particulates in a sample, comprising:
    (i) introducing the particulates into a plasma; and
    (ii) measuring a potential difference between a common electrode and each of a plurality of indicator electrodes.

2. The method of claim 1, wherein the common and indicator electrodes are positioned in the plasma.

3. The method of claim 1, wherein all the indicator electrodes are made from the same material.

4. The method of claim 1, wherein at least one indicator electrode is made from a material different from a material from which at least one of the other indicator electrodes is made.

5. The method according to claim 1, wherein the plasma is selected from the group consisting of glow discharge plasma (direct current (DC) or radio frequency ((RF)), capacitively coupled plasma (RF), inductively coupled plasma (RF), wave heated plasma (RF or microwave frequency (MW)), flame plasma, arc discharge plasma, corona discharge plasma, dielectric barrier discharge plasma and capacitive discharge plasma (RF).

6. The method according to claim 1, wherein the plasma is a flame plasma.

7. The method of claim 6, wherein the introduction of the particulates into the flame plasma comprises:
 (a) creating a product stream comprising the particulates and a combustible gaseous stream; and
 (b) igniting the product stream to form the flame plasma.

8. The method of claim 1, wherein each indicator electrode independently has the dimensions of about 0.1 mm$^2$ to about 50.0 mm$^2$.

9. The method of claim 1, wherein the plurality of indicator electrodes is a multi electrode array.

10. The method of claim 1, wherein the particulates are selected from biological and non-biological species.

11. A potentiometric apparatus for the detection of particulates in a sample, comprising:
 (i) a means arranged to introduce the particulates into a plasma; and
 (ii) a common electrode and at least three indicator electrodes; wherein the electrodes are positioned to measure the potential difference between the common electrode and each of the at least three indicator electrodes in the plasma.

12. The apparatus of claim 11, wherein the plasma is a plasma selected from the group consisting of glow discharge plasma (direct current (DC) or radio frequency ((RF)), capacitively coupled plasma (RF), inductively coupled plasma (RF), wave heated plasma (RF or microwave frequency (MW)), flame plasma, arc discharge plasma, corona discharge plasma, dielectric barrier discharge plasma and capacitive discharge plasma (RF).

13. The apparatus of claim 11, wherein the plasma is a flame plasma.

14. The apparatus of claim 13, comprising a means for providing a combustible gaseous stream, wherein the combustible gaseous stream is ignitable to produce the flame plasma.

15. The apparatus of claim 14, wherein the means arranged to introduce the particulates comprises a means for creating a product stream comprising the particulates and the combustible gaseous stream.

16. The apparatus of claim 11, wherein all the indicator electrodes ar made from the same material.

17. The apparatus of claim 11, wherein at least one indicator electrode is made from a material different from a material from which at least one of the other indicator electrodes is made.

18. The apparatus of claim 11, wherein each indicator electrode independently has the dimensions of about 0.1 mm$^2$ to about 50.0 mm$^2$.

19. The apparatus according to claim 11, wherein the plurality of indicator electrodes is a multi electrode array.

* * * * *